United States Patent [19]

Kwan

[11] Patent Number: 5,753,453
[45] Date of Patent: May 19, 1998

[54] STABLE SINGLE LIQUID REAGENT FOR THE DETERMINATION OF CARBON DIOXIDE IN SERUM

[75] Inventor: Shing Fai Kwan, Ventura, Calif.

[73] Assignee: Ivan E. Modrovich, Camarillo, Calif.

[21] Appl. No.: 398,908

[22] Filed: Mar. 6, 1995

Related U.S. Application Data

[63] Continuation of Ser. No. 994,192, Dec. 21, 1992, abandoned.

[51] Int. Cl.$^6$ ............... C12Q 1/32; C12Q 1/48; G01N 33/50
[52] U.S. Cl. ............... 435/15; 435/26; 435/74; 435/25; 436/68; 436/63; 436/4; 436/904
[58] Field of Search ............... 435/15, 26, 25, 435/4; 436/68, 63, 74, 904

[56] References Cited

U.S. PATENT DOCUMENTS

| | | | |
|---|---|---|---|
| 3,963,578 | 6/1976 | Aitken et al. | 435/15 |
| 3,974,037 | 8/1976 | Adams | 435/15 |
| 5,112,740 | 5/1992 | Nealon et al. | 435/15 |
| 5,429,930 | 7/1995 | Cunningham et al. | 435/15 |
| 5,480,777 | 1/1996 | Cunningham et al. | 435/15 |
| 5,514,538 | 5/1996 | Evans | 435/15 |

*Primary Examiner*—John Kight
*Assistant Examiner*—Louise Leary
*Attorney, Agent, or Firm*—Christie, Parker & Hale, LLP

[57] ABSTRACT

A stable single reagent for the determination of carbon dioxide in serum is provided as an aqueous solution of diagnostically amounts and NADH and/or NADPH, and a stabilizing system therefore reactively stabilized PEPC and a substrate for reacting with bicarbonate ion under alkaline conditions in the presence of PEPC.

21 Claims, 2 Drawing Sheets

STABLE SINGLE LIQUID REAGENT FOR THE DETERMINATION OF CARBON DIOXIDE IN SERUM

CROSS-REFERENCE TO RELATED APPLICATION

This is a continuation of application Ser. No. 07/994,192 filed Dec. 21, 1992, now abandoned.

FIELD OF THE INVENTION

The invention relates to a stable single liquid reagent composition for the determination of carbon dioxide in sera and other body fluids.

BACKGROUND OF THE INVENTION

The determination of total $CO_2$ of sera in conjunction with other clinical and laboratory information is necessary for the evaluation of acid-base status. A high $CO_2$ content may be observed in compensated respiratory acidosis and metabolic alkalosis. A low $CO_2$ content may be observed in compensated respiratory alkalosis and metabolic acidosis.

Total carbon dioxide in sera or plasma exists in two major chemical forms, dissolved $CO_2$ and bicarbonate ($HCO_3^-$) anion. The minor forms are carbonic acid and carbonate ion and carbamino derivatives of plasma proteins.

A method used to measure total carbon dioxide by chemical analyzers involve the quantitative conversion of all carbon dioxide forms to $HCO_3^-$ by adding alkali to the serum. Bicarbonate is then enzymatically linked to NADH consumption and quantified spectrophometrically by the reactions:

(1)

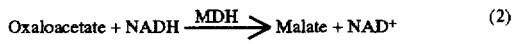
(2)

wherein PEPC is phosphoenolpyruvate carboxylase and MDH is malate dehydrogenase. The decrease in absorption at 340 nm is related to serum concentration of $CO_2$. More detail regarding this various other methods for determining carbon dioxide in sera are described in *Clinical Chemistry*, Kaplan, et al., The C. V. Mosby Company (1984) at pp. 1056–58, incorporated herein by reference.

The diagnostic reagents for the determination of $CO_2$ and other constituents of sera have often been plagued with limited stability. In general, commercial products have been limited to compositions that required at least one part to be lyophilized. Once reconstituted the reagent composition has a limited stability at normal storage of 2° to 10° C., and an even shorter stability at room temperature.

For a $CO_2$ reagent the instability has been caused by two major factors: rapid degradation of NADH to NAD and rapid loss of enzymatic activity of phosphoenolpyruvate carboxylase (PEPC).

U.S. Pat. No. 5,116,728 to Crowther, et al. ("'728" herein) by reference discloses a two-component composition which, when combined, forms a diagnostic reagent for the detection of carbon dioxide in serum. Crowther, et al describes the utilization of a stabilization reaction to convert the degradation product of NADH, NAD, back to NADH. This is a specific application of U.S. Pat. No. 4,394,449 to Modrovich ("'449" herein) incorporated herein by reference.

Modrovich '449 teaches that labile conenzymes can be stabilized by regenerative reactions. The stabilized coenzyme solutions are prepared by adding a regenerative enzyme to the aqueous solution containing the coenzyme to be regenerated. In addition to adding the regenerative enzyme, the substrate with which the enzyme exerts catalytic action is also added. The addition of the regenerative enzyme and substrate to the coenzyme solution or assay system provides regeneration of the coenzyme thus, in effect, a stabilization of the coenzyme. To the coenzyme solution or assay system can also be added the coenzyme form such as the reduced or oxidized which, upon interaction with the substrate and enzyme, produces the other coenzyme form, i.e., oxidized or reduced respectively. For example, with the coenzyme NAD or NADH, if it is desired to stabilize NADH, then NAD can be added to the solution along with the appropriate enzyme and substrate for generating NADH. The presence of the coenzyme conversion form aids in the regeneration of the coenzyme as its presence starts to generate the coenzyme as soon as the coenzyme begins to convert or degrade.

The '728 patent describes a two component reagent system for the detection of $CO_2$. The first component contains a first diagnostic substrate for a first diagnostic enzyme, a reduced form of the coenzyme, optionally a buffer, a stabilizer enzyme which reduces the oxidized form of the coenzyme, a substrate for the stabilizer enzyme, optionally the oxidized form of the coenzyme, a rate-limiting amount of one of the first or second diagnostic enzymes, and a non-rating-limiting amount of the other diagnostic enzyme. The second component contains the two diagnostic enzymes.

The diagnostic enzymes are known to be malate dehydrogenase (MDH) and phosphoenolpyruvate carboxylase (PEPC). In the specification of Crowther, et al. it is discussed that MDH is the rate-limiting diagnostic enzyme as PEPC is unstable.

The assignee of the instant invention has long promoted the use of liquid reagents for the determination of various constituents in serum and plasma. The quest has always been to develop a single reagent that is one where all the constituents may be combined in a solution or emulsion at the time of manufacture, eliminating, as in the case of lyophilized assay ingredients, the errors in reconstituting an assay solution at the time of use and in the use of multiple component compositions, the errors which may occur in combining the components. This allows complete quality control to occur at the time of manufacture and eliminates or minimizes the possibility of error on the part of the user in formulating an assay composition at the time of use.

For a single reagent composition to be marketable, it must have a stability sufficient to enable storage at point of manufacture, shipment to anywhere in the world and storage at destination until use and stability during use. Often, the quest is to formulate a solution which has a minimum lifetime of 12 to 18 months at 2° to 10° C. which corresponds to 3 days at 41° C. for accelerated stability testing, commonly referred to as stress tests.

The ability to form a single reagent solution also enhances the ability to stabilize reconstituted lyophilized compositions and condensed multicomponent systems. This ability to enhance stability of a reconstituted or combined multicomponent system reduces the volume of wasted reagent that cannot be used prior to its deterioration.

A need therefore exists to provide a single, liquid stable carbon dioxide reagent. This reagent system will eliminate the need for multi-component reagent systems. It will also eliminate the need for rate-limiting diagnostic enzymes to be utilized to further stabilize NADH.

SUMMARY OF THE INVENTION

In accordance with the instant invention there is provided a stable single liquid reagent for determination of carbon dioxide in sera. The reagent is formulated as an aqueous solution of a first diagnostic enzyme which is a reactively stabilized phosphoenolpyruvate carboxylase (PEPC), a first diagnostic substrate for phosphoenolpyruvate carboxylase preferably phosphoenolpyruvate (PEPC), a second diagnostic enzyme capable of catalyzing a reaction between a product of the first diagnostic reaction and the substrate for the second diagnostic reaction, preferably malate dehydrogenase, a second diagnostic substrate which is the reduced form of nicotinamide adenine dinucleotide (NADH) or nicotinamide adenine dinucleotide phosphate (NADHP), reagents for the stabilization of NADH which include at least one stabilizing enzyme which in the presence of its corresponding substrate is capable of converting the oxidized form of nicotinamide adenine dinucleotide (NAD) or its phosphate NADP to the reduced form NADH or NADPH at a rate to sufficiently stabilize NADH or NADPH without significantly interfering with the diagnostic reaction. A cofactor is desirable to provide further enhance the stability of the reactive stabilized PEPC preferably d-biotin. Optionally a polyol and/or gelatin can also be added to further enhance the stability of PEPC. The solution has a pH of from about 5 to about 11, preferably from about 8.0 to about 9.5. Optionally, the pH is maintained by the addition of a buffer that is capable of buffering in the acceptable pH range Zwitterionic buffers are preferably used. An antimicrobial stabilizer may also be optionally added and sterile conditions can be utilized during handling to reduce the risk of contamination.

The ingredients which react to determine $CO_2$ are provided in a diagnostically effective amount. That is concentration are tailored to the operating characteristics of the diagnostic equipment in which they are used. Diagnostic equivalence are designed to complete an analysis within 10 minutes at 37° C., 12 minutes at 30° C. or 15 minutes at 20° C. The standard temperature of operation in the United States is 37° C.

The stable single liquid reagents of the invention have a shelf life in excess of 18 months at 2° to 10° C. which corresponds to a stability of more than 3 days at 41° C.

DETAILED DESCRIPTION

Figure 1:
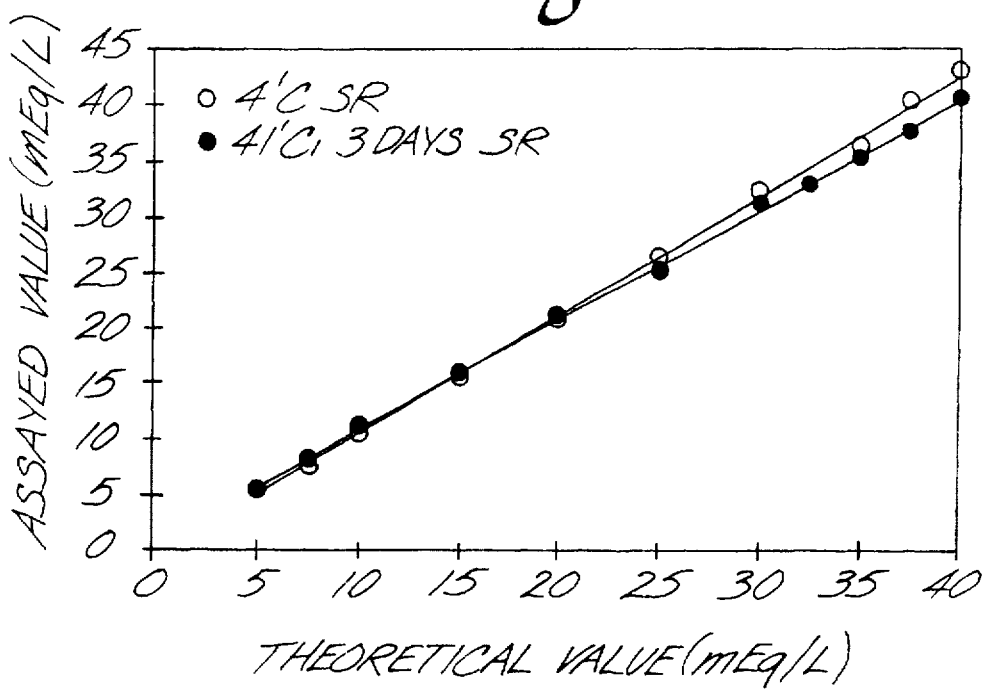
FIG. 1 correlates assayed value against theoretical value of $CO_2$ using a NERL standard for the $CO_2$ assay composition as formulated and after stress at 41° C. for 3 days, the data for which is reported in Table 2.

The present invention is directed to a single stable liquid reagent for the determination of carbon dioxide in sera and other body fluids. Using the single liquid reagent of the instant invention, carbon dioxide is converted to bicarbonate in an alkaline diagnostic medium, the bicarbonate in turn converts a first substrate preferably phosphoenolpyruvate in the presence of PEPC to a reactive product preferably oxyloacetate and an inorganic phosphate. In the presence of a second diagnostic enzyme preferably MDH or NADPH and NADH, the product oxaloacetate is reduced to malate and NADH or NADPH is oxidized to NAD. The conversion of NADH to NAD or NADPH to NADP can be monitored at a wavelength of about 340 nm.

The conversion rate is proportionate to the concentration of $CO_2$ in the sample. End point and rate type reactions can be utilized in the measurement of $CO_2$. In either event, the basic reaction for determining the $CO_2$ may be written as:

(1)

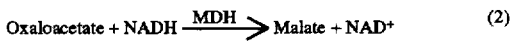
(2)

It is well known that NADH or NADHP are highly unstable labile substrates which will degrade to $NAD^+$ in an aqueous solution. The stabilization reaction is based on providing a driving force to reform NADH from $NAD^+$. As disclosed in the '449 patent, any enzyme or enzymatic system and its corresponding substrate which are involved in the catalysis of a reaction forming NADH from $NAD^+$ can be utilized to stabilize NADH or NADHP. Without limiting examples of such systems include:

| ENZYME | SUBSTRATE |
| --- | --- |
| Hexokinase/Glucose-6-Phosphate Dehydrogenase | Glucose/ Glucose-6-phosphate |
| Glucose Dehydrogenase | Glucose |
| Lactate Dehydrogenase | Lactate |
| Sorbitol Dehydrogenase | Sorbitol |
| Galactose Dehydrogenase | Galactose |
| Alcohol Dehydrogenase | Ethanol |
| Glutamate Dehydrogenase | Glutamate |
| Glycerol Phosphate Dehydrogenase | Dihydroxy-acetone phosphate |

Other enzyme—substrate combinations may also be used. The hexokinase/Glucose-6-Phosphate Dehydrogenase-glucose combination is preferably used to stabilize NADH in the compositions of this invention.

If the rate of reaction of converting $NAD^+$ to NADH is too fast so as to convert $NAD^+$ to NADH immediately, then the reagent could not be used for a $CO_2$ reaction because it would be impossible to measure the rate or degree of conversion of NADH to $NAD^+$.

It is important therefore, that the rate of converting $NAD^+N$ to NADH or NADPH to $NADP^+$ be approximately the rate of NADH or NADHP degradation on storage and not include the rate of conversion of NADH or NADHP to $NAD^+$ or $NADP^+$ caused by the diagnostic reaction, set forth above and the amount of enzyme—substrate employed is just that required to maintain NADH as the record substrate.

It is known that hexokinase is activity controlled by magnesium. By controlling the amount of magnesium present, the activity of hexokinase can be controlled thereby controlling the conversion of glucose to glucose-6-phosphate which in turn controls the rate of $NAD^+$ conversion to NADH.

Magnesium is preferably added as magnesium acetate and its availability can be further controlled by the use of chelating agents such as ethylenediamine tetraacetic acid (EDTA).

Another way of controlling the stabilizing reaction is by controlling the amount of stabilizing enzyme added to the solution or the amount of corresponding substrate added to the solution. Such techniques are well known to any one with ordinary skill in the art and illustrated in Table 1 listing the components of the preferred composition of this invention.

A key requirement of the invention is to employ a reactively stabilized PEPC. The process for its reactive stabilization is described below.

Phosphoenol pyruvate carboxylase (PEPC) was stabilized forming a solution of 20 mg/ml of PEPC in an aqueous base containing 50 mg/ml bovine serum albumin (BSA). 10 mg/ml 2-amino-2hydroxy methyl-1,3-propanediol (TRIS) and 50 mg/MgOAc without pH adjustment.

Solutions of 1-ethyl-3-(dimethylaminopropyl)-cabodimide) (EDAC) and polysuccinylated lysine (PSL) in dimethylsulfoxide (DMSO) at respective concentrations of 100 mg/ml and 20 mg/ml were formed.

The PSL solution was added to the PEPC solution dropwise with stirring over an ice bath followed by the addition of the EDAC solution. mixture was stored at 40° C. for 4 days and incubated for 2 days at 350° C.

More generally, PEPC is reactively stabilized by reacting it with a biostabilizer in an aqueous media in the presence of a condensing or linking agent. In this technique there is first provided a solution of PEPC under suitable refrigerated conditions, i.e., greater than 0° and up to about 10° C., to which a solution of a biostabilizer is added slowly at a reduced temperature of greater than 0° and up to about 10° C. with mixing. Following this, there is added in a solution of a condensing agent which enhances the formation of covalent bonds between PEPC and the biostabilizer. The condensing agent may cause and/or enter into the reaction and become part of the soluble stabilized product.

By the term "biostabilizer" there is meant a biological material which will enter into a cross-linking covalent reaction with a labile analyte, here PEPC directly or through a condensing agent to immobilize the analyte in an active form.

By the term "condensing or linking agent" there is meant a compound which will cause or enter into a covalent cross-linking reaction involving the biostabilizer and labile analyte.

The biostabilizers which are employed to bind to labile analytes are water soluble, hydrophilic compounds which inherently contain or may be modified to contain one or more sites which are reactive with sites on the analyte. The biostabilizers include biopolymers such as polyarginine, poly-dl-lysine, poly-l-lysine, poly-dl-aspartate, poly-l-aspartate, poly-l-glutamic acid, polysuccinylated lysine (PSL) and the like.

The condensing agent initiates and may enter into the cross-linking reaction. They are molecules which contain appropriate reactive groups to initiate covalent linkage between the biostabilizer and the labile analyte. The condensing agent may activate and/or enter into the reaction, e.g., serve as a cross-linking group between the biostabilizer and analyte.

The covalent linkage can either be between the same functional groups or different functional groups. there are three types of condensing reagents, namely: homobifunctional, heterobifunctional, and zero-length reagents. There are hundreds of reagents which fit these categories.

In homobifunctional reagents the functional groups involved in the reaction between the labile analyte and the biostabilizer are the same. Heterobifunctional reagents contain two dissimilar reactive groups of different specificities. Zero-length reagents are a special class of compounds. They induce direct joining of tow chemical groups of proteins without introducing any additional atoms or molecules.

The reactive stabilization technique allows PEPC to retain its enzymatic activity in an aqueous solution. The presently preferred technique for stabilization of PEPC is described in Example 1 of this application.

A cofactor may be used to further enhance the stability of PEPC. A preferred cofactor is d-biotin. There may be employed a polyol such as sorbitol, mannitol, trehalose and the like, and/or gelatin to further enhance the stability of PEPC. The assay solutions of this invention have a pH of from about 5 to about 11, preferably from about 8.0 to about 9.5. Solution pH may be maintained by the addition of a Zwitterionic buffer that is capable of buffering in the acceptable pH range. Such buffers include (2-[(2-amino-2-oxoethyl)-amino]-ethanesulfonic acid, (N-[2-acetamido]-2-iminodiacetic acid, (3-[1,1-dimethyl-2-hydroxyethyl) amino]-2-hydroxypropanesulfonic acid, (N,N-bis[2-hydroxyethyl]-2-aminoethanesulfonic acid, (N,N-bis[2-hydroxyethyl]glycine, (3-[cyclohexylamino]-1-propanesulfonic acid, (2N-[cyclohexylamino]-ethanesulfonic acid, (N-[2-morpholino]ethanesulfonic acid, (3-[N-morpholino]propanesulfonic acid), (3-[N-tris (hydroxymethyl)methylamino]-2-hydroxypropanesulfonic acid), tris[hydroxymethyl]aminomethan, and the like, and mixtures thereof. Further an antimicrobial stabilizer may optionally be added. Such antimicrobial agents include sodium azide, antibiotics, and the like. Sterile conditions can be utilized during handling to reduce the risk of contamination.

While solutions of the instant invention may be provided as an acid pH it is understood that the assay is conducted under alkaline conditions. This may be the result of combining the assay solution with the sample or by alkalizing the mixture.

The preferred solutions are an aqueous solution comprising: about 0.1 to about 100 g/l, preferably about 0.4 g/l, TRIS; about 0.001 to about 10, preferably about 0.2 g/l of EDTA, from about 0.1 to about 100 g/l, preferably about 2 g/l, glucose; from about 0.1 to about 100 g/l, preferably about 5 g/l, substrate; from about 0.01 to about 50 g/l, preferably about 0.5 g/l, of ATP; from about 0.01 to about 20 g/l, preferably about 0.4 g/l, of sodium azide as an antimicrobial agent; from about 0.01 to about 5 g/l, preferably about 0.244 g/l, of Vitamin H; from 0 to about 200 ml/l, preferably about 40 ml/l, of a mixture of sorbitol and gelatin; from about 0.6 to about 2.0 g/l, preferably about 1.3 g/l, of NADH; from about 2 to about 2,000 U/l at 25° C., preferably about 200 U/l, at 25° C. of hexokinase; from 0.1 to 2,000 U/l preferably about 20 U/l, at 25° C. of G6PDH; from about 200 to about 5,000, preferably about 500 U/l, of MDH; from about 200 to about 2,000 U/l, preferably about 500 U/l, of PEPC at 37°O C.; said solution having a pH of from about 8.75 to about 9.25.

Table 1 shows specific formulations in accordance with the instant invention and found to be viable for the determination of $CO_2$ by rate or end point methods. In the Table 1, A and C are a five-times concentrated solution used with analyzers which dilute the assay composition four parts water and one part assay solution during use. In formulating the compositions, the stabilized PEPC is stabilized according to Example 1.

Although specific formulations are given the essential ingredients are provided in a diagnostically effective amount. By the term "diagnostically" effective amount there is meant concentrations which enable the assay to go to completion within 10 minutes at 37° C. (body temperature), 12 minutes at 30° C. or 15 minutes at 25° C., the normal design operating parameters for commercial mass spectrophotometers.

All results shown in Examples 2, 3 and 4 were obtained utilizing a Roche Cobas Bio analyzer. For formulations A and C the assay compositions were manually diluted four parts water and one part assay composition prior to use. All of the reactions were run as end point assays, except Example 6 which was run as a rate assay. The parameters of the assays were defined as follows:

|  | RATE ASSAY | END POINT |
|---|---|---|
| Temperature | 37° C. | 37° C. |
| Wavelength (closest to 340 nm) | 380 nm | 380 nm |
| Sample Volume | 3 μl | 3 μl |
| Diluent Volume | 10 μl | 10 μl |
| Reagent Volume | 300 μl | 300 μl |
| Time of first read | 40 sec | 0.5 sec |
| Time of second read | 150 sec | 600 sec |

A 25 mEg/l NERL standard was utilized as the calibrator for each assay.

TABLE 1

| | Given in amount per liter | | | |
|---|---|---|---|---|
| Ingredient | A | B | C | D |
| TRIS | 2 g | 0.4 g | 2 g | 0.4 g |
| EDTA.Na$_2$ | 1 g | 0.2 g | 1 g | 0.2 g |
| glucose | 10 g | 2 g | 10 g | 2 g |
| PEP (CHA)$_3$ | 50 g | 10 g | 20 g | 5 g |
| ATP.Na$_2$ | 2.5 g | 0.5 g | 2.5 g | 0.5 g |
| MgAc.$_4$H$_2$O | 3.2 g | 0.64 g | 3.2 g | 0.64 g |
| NaN$_3$ | 2 g | 0.4 g | 2 g | 0.4 g |
| d-biotin | — | — | 1.222 g | 0.244 g |
| SB | 200 ml | 40 ml | 40 ml | 40 ml |
| NADH.Na$_2$ | 7 g | 1.4 g | 6.5 g | 1.3 g |
| HK (25° C.) | 1000 U | 200 U | 1000 U | 200 U |
| G6PDH (25° C.) | 100 U | 20 U | 100 U | 20 U |
| MDH (37° C.) | 2500 U | 1000 U | 2500 U | 500 U |
| PEPC (37° C.) | 2500 U | 1000 U | 2500 U | 500 U |
| pH | 9.25 | 9.25 | 9.00 | 8.75 |

TRIS = (tris) [hydroxymethyl]aminomethane)
EDTA = ethylenediaminetetraacetic acid
PEP (CHA)$_3$ = phosphoenolpyruvate tri(cyclohexylammonium) salt
ATP = adenosine-5'-triphosphate
MgAc$_3$ = magnesium acetate
NaN$_3$ = sodium azide
NADH = nicotinamide adenine dinucleotide reduced
HK = hexokinase
G6PDH = glucose-6-phosphate dehydrogenase
MDH = malte dehydrogenase
PEPC = phosphoenolpyruvate carboxylase

EXAMPLE 1 AND CONTROL 1

Stabilization of Phosphoenolpyruvate Carboxylase (PEPC)

There was formed a solution of 20 mg/ml of PEPC by dissolving PEPC in an aqueous base containing 50 mg/ml bovine serum albumin (BSA), 10 mg/ml TRIS and 50 mg/ml magnesium aspartate without pH adjustment.

Solutions of 1-ethyl-3-(3-dimethylaminopropyl) carbodiimide and polysuccinylated lysine (PSL) in DMSO at respective concentrations of 100 mg/ml and 20 mg/ml were formed.

The PSL solution was added to the PEPC solution dropwise with stirring over an ice bath followed by the addition of the EDAC solution, mixture was stored at 4° C. for 4 days and incubated at 2 days at 35° C.

Table 2 compares the stability of the PEPC in pilot B from Table 1. The control is PEPC added to pilot B without stabilizing first.

TABLE 2

Performance of Stabilized PEPC in CO$_2$ single liquid reagent

|  | % PEPC after 1 day at 4 and 41° C. % PEPC at 4° C. | | % PEPC after 3 days at 4 and 41° C. % PEPC at 4° C. | |
|---|---|---|---|---|
|  | 4° C. | 41° C. | 4° C. | 41° C. |
| Example 1 | 100% | 95% | 100% | 90% |
| Control 1 | 100% | 0% | 100% | 0% |

EXAMPLE 2

Composition D from Table 1 was used to determine the ability to assay for CO$_2$ in serum as formulated (4° C.) and when stressed for 3 days at 41° C. The results are reported in Table 3 using an industrial NERL standard. The results establish that there is less than a 10% difference between the 4° C. reagent and the reagent that had been stressed for 3 days at 41° C. This would indicate a projected long reagent stability at 4° C. The data is plotted in FIG. 1 and reported in Table 3.

TABLE 3

| NERL Std. | Theoretical Value (mEq/L) | Assayed Value (mEq/L) | |
|---|---|---|---|
|  |  | by 4° C. SR | by 41° C. SR |
| 1 | 5.0 | 5.75 | 5.28 |
| 2 | 7.5 | 7.67 | 8.03 |
| 3 | 10.0 | 10.32 | 11.09 |
| 4 | 15.0 | 15.45 | 15.89 |
| 5 | 20.0 | 20.78 | 21.16 |
| 6 | 25.0 | 26.41 | 25.15 |
| 7 | 30.0 | 32.41 | 31.28 |
| 8 | 32.5 | 33.05 | 32.88 |
| 9 | 35.5 | 36.05 | 35.39 |
| 10 | 37.5 | 40.44 | 37.68 |
| 11 | 40.0 | 43.14 | 40.60 |

In addition the Initial Absorbance at 380 nm for both the 4° and 3 days at 41° C. reagents were measured. This is important as the assay is based on measuring the conversion of NADH to NAD$^-$ as a function of CO$_2$ concentration in a sample. Also, the stability of MDH and stabilized PEPC was determined after stress. The results are in Table 4.

TABLE 4

| | Initial Absorbance | MDH (37° C.) | PEPC (37° C.) |
|---|---|---|---|
| 4° C. | 2.1317 | 683 U/l | 643 U/l |
| 41° C. | 2.0849 | 624 U/l | 601 U/l |
| % Change | −2.2% | −8.4% | −6.5% |

This shows the inherent stability of MDH in this reagent composition and the gained stability of PEPC by first stabilizing by the method illustrated in Example 1.

EXAMPLE 3

Figure 2:
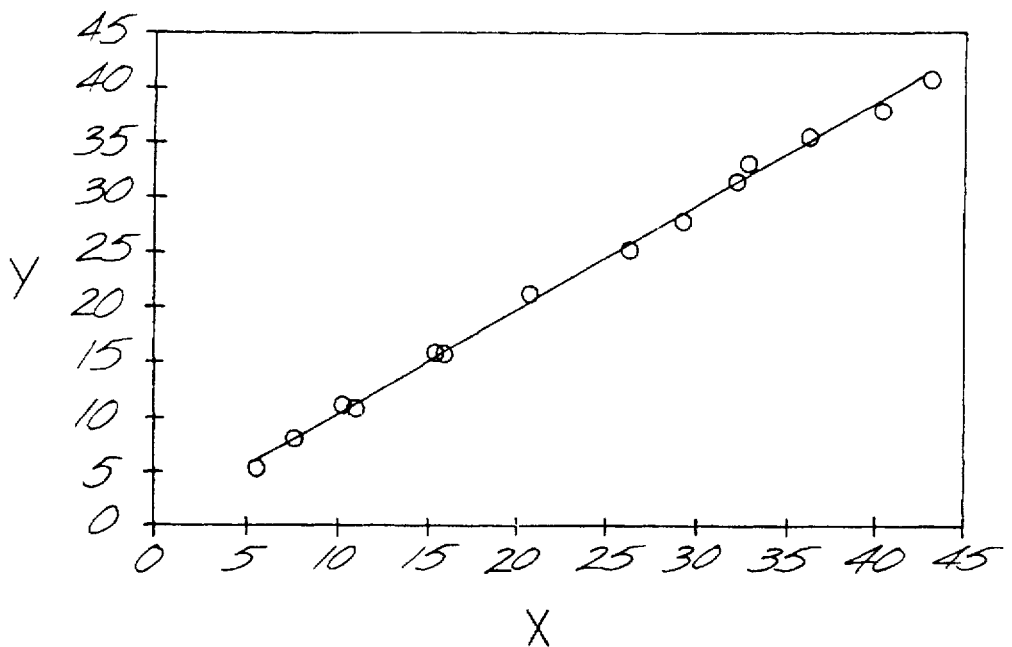
FIG. 2 is a plot of $CO_2$ recovery as formulated (X) against the composition stressed at 41° C. for 3 days in mEq/L (Y). The correlation coefficient is 0.9985. The data is contained in Table 4.

In the next study, the correlation between Composition D from Table 1 as formulated to the composition after stress at 41° C. for 3 days was determined using NERL standards and chemTRAK controls at levels 1, 2, and 3. Values for the correlation determination are reported in Table 5 and plotted in FIG. 2. The correlation was 0.9985 where a perfect correlation would be 1.

TABLE 5

| Sample | | Assayed value by 4° C. | (mEq/L) by 41° C. |
|---|---|---|---|
| NERL | 1 | 5.57 | 5.28 |
| | 2 | 7.67 | 8.03 |
| | 3 | 10.32 | 11.09 |
| | 4 | 15.45 | 15.89 |
| | 5 | 20.78 | 21.16 |
| | 6 | 26.41 | 25.15 |
| | 7 | 32.40 | 31.28 |
| | 8 | 33.05 | 32.88 |
| | 9 | 36.50 | 35.39 |
| | 10 | 40.44 | 37.68 |
| | 11 | 43.13 | 40.60 |
| chemTRAK | L1 | 11.05 | 10.75 |
| | L2 | 15.96 | 15.64 |
| | L3 | 29.28 | 27.81 |

EXAMPLE 4

Figure 3:
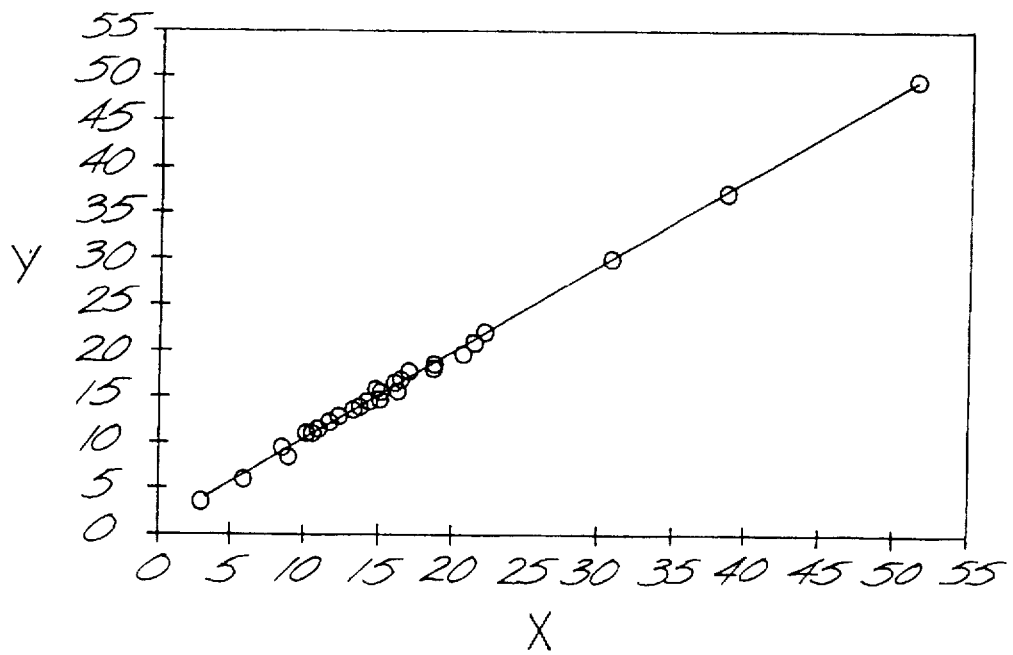
FIG. 3 is a plot of $CO_2$ recovery from human serum from 30 individuals using the assay composition as formulated (X) and stressed for 3 days at 41° C. (Y). The data is from Table 5.

Following the same procedure as Example 3, there was used instead human serum from 30 different patients and again, as shown in FIG. 3, the correlation was 0.9984 for the study. The pool was several human samples combined. The resultant $CO_2$ concentration was denoted "as is". The 1/5th, 2/5ths, 3/5ths and 4/5ths samples are dilutions of the pool with saline. This was done to-evaluate the dilutability factor of the reagent. This is an important step when evaluating the marketability of a-reagent.

The spiked pool 1, 2, 3, and 4 were samples from the "as is" pool that were spiked with increasing concentrations of $CO_2$ by the addition of sodium bicarbonate.

The results are shown in TABLE 6.

TABLE 6

| Sample | Assayed value by 4'C SR | (mEq/L) by 41' C SR |
|---|---|---|
| 1 | 12.42 | 13.05 |
| 2 | 15.18 | 15.51 |
| 3 | 16.36 | 16.29 |
| 4 | 20.83 | 19.47 |
| 5 | 14.99 | 15.06 |
| 6 | 13.39 | 13.46 |
| 7 | 10.60 | 10.92 |

TABLE 6-continued

| Sample | Assayed value by 4'C SR | (mEq/L) by 41' C SR |
|---|---|---|
| 8 | 11.19 | 11.86 |
| 9 | 13.50 | 14.09 |
| 10 | 13.85 | 14.05 |
| 11 | 13.68 | 13.58 |
| 12 | 14.35 | 14.73 |
| 13 | 14.10 | 14.37 |
| 14 | 15.07 | 14.75 |
| 15 | 18.91 | 18.52 |
| 16 | 17.05 | 17.79 |
| 17 | 14.35 | 14.76 |
| 18 | 18.87 | 18.01 |
| 19 | 14.91 | 15.81 |
| 20 | 11.73 | 12.16 |
| 21 | 16.51 | 16.78 |
| 22 | 14.80 | 15.03 |
| 23 | 21.54 | 20.61 |
| 24 | 16.47 | 15.44 |
| 25 | 16.19 | 16.61 |
| 26 | 11.10 | 11.50 |
| 27 | 10.04 | 11.08 |
| 28 | 11.27 | 12.14 |
| 29 | 8.67 | 9.34 |
| 30 | 8.61 | 9.34 |
| 1/5 | 3.01 | 3.46 |
| 2/5 | 5.94 | 5.82 |
| 3/5 | 8.85 | 8.57 |
| 4/5 | 10.95 | 11.26 |
| spiked pool | | |
| 1 | 22.37 | 22.04 |
| 2 | 30.93 | 30.00 |
| 3 | 38.64 | 37.19 |
| 4 | 51.44 | 49.49 |

EXAMPLE 5

Figure 4:
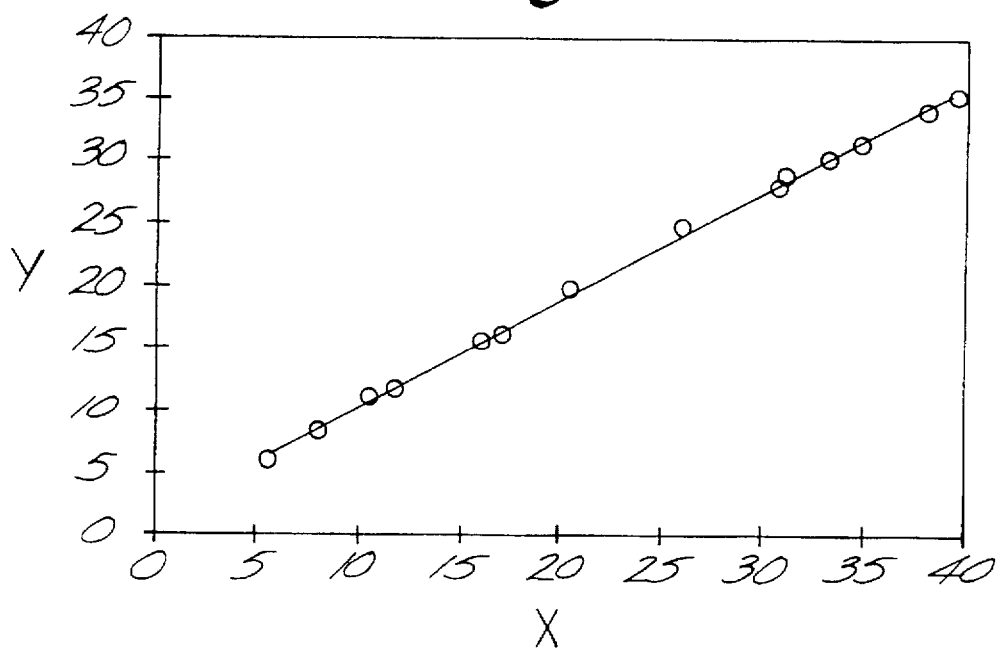
FIG. 4 is plot of $CO_2$ recovery using the NERL standard and 3 chemTRAK levels per recovery using the 5× composition of Table 1 as formulated (X) and after stress for 3 days at 41° C. (Y).

Again, the NERL and ChemTRAK controls were used to correlate the composition as formulated and after stress for 3 days at 41° C. for composition C in Table 1. The results, reported in Table 7 and plotted in FIG. 4, established a correlation coefficient of 0.9991. chemTRAK is a commercial product of Medical Analysis Systems, Inc.

TABLE 7

| Sample | | Assayed Value by 4° C. | (mEQ/L) by 41° C. |
|---|---|---|---|
| NERL | 1 | 5.64 | 6.04 |
| | 2 | 8.10 | 8.38 |
| | 3 | 10.59 | 11.16 |
| | 4 | 16.20 | 15.64 |
| | 5 | 20.50 | 19.85 |
| | 6 | 26.09 | 24.87 |
| | 7 | 31.21 | 28.90 |
| | 8 | 33.34 | 30.24 |
| | 9 | 34.91 | 31.46 |
| | 10 | 38.23 | 33.98 |
| | 11 | 39.61 | 35.15 |
| chemTRAK | L1 | 11.89 | 11.72 |
| | L2 | 17.11 | 16.20 |
| | L3 | 30.86 | 27.92 |

In addition the Initial Absorbance at 380 nm of both the 4° C. and 3 days at 41° C. reagents were measured. Also, the stability of MDH and stabilized PEPC was determined after stress. Prior to measuring the reagent was diluted one part reagent plus four parts water. The results are in Table 8.

TABLE 8

| | Initial Absorbance | MDH (37° C.) | PEPC (37° C.) |
|---|---|---|---|
| 4° C. | 1.8818 | 580 U/l | 589 U/l |
| 41° C. | 1.6883 | 507 U/l | 545 U/l |
| % Change | −11% | −12.5% | −7.5% |

Again, this shows good stability for both the native MDH and the stabilized PEPC.

EXAMPLE 6

Following the same procedure as in Example 5, except a rate assay instead of an end point assay was done, there was used human serum from 30 different patients and again, the correlation was 0.9969 for the study. The pool was several human samples combined. The resultant $CO_2$ concentration was denoted "as is". The ⅕, ⅖ ⅗, and ⅘ samples were dilutions of the pool with saline.

The spiked pool 1, 2, and 3 were samples from the "as is" pool that were spiked with increasing concentrations of $CO_2$ by the addition of sodium bicarbonate.

The results are shown in Table 9.

TABLE 9

| Sample | Assay value | (mEq/L) |
|---|---|---|
| 1 | 15.99 | 15.15 |
| 2 | 17.51 | 16.48 |
| 3 | 13.61 | 12.54 |
| 4 | 18.78 | 17.55 |
| 5 | 16.06 | 15.35 |
| 6 | 11.81 | 11.31 |
| 7 | 22.53 | 20.81 |
| 8 | 16.01 | 14.72 |
| 9 | 18.84 | 17.89 |
| 10 | 16.72 | 15.81 |
| 11 | 12.15 | 11.20 |
| 12 | 19.03 | 17.24 |
| 13 | 17.77 | 16.67 |
| 14 | 12.37 | 11.94 |
| 15 | 13.06 | 12.44 |
| 16 | 22.08 | 21.36 |
| 17 | 12.33 | 12.39 |
| 18 | 15.74 | 14.53 |
| 19 | 16.27 | 15.35 |
| 20 | 13.87 | 13.15 |
| 21 | 14.10 | 13.57 |
| 22 | 17.30 | 16.21 |
| 23 | 16.83 | 15.78 |
| 24 | 15.15 | 14.35 |
| 25 | 14.86 | 14.79 |
| 26 | 16.35 | 16.27 |
| 27 | 13.26 | 13.37 |
| 28 | 16.42 | 16.33 |
| 29 | 16.90 | 16.71 |
| 30 | 21.28 | 21.12 |
| ⅕ | 3.15 | 3.54 |
| ⅖ | 6.79 | 7.06 |
| ⅗ | 10.39 | 10.32 |
| ⅘ | 13.43 | 13.09 |
| "as is" | 15.07 | 15.67 |
| Spiked pool | | |
| 1 | 23.45 | 23.36 |
| 2 | 35.81 | 34.00 |
| 3 | 45.78 | 42.10 |

Again, this shows good stability for both the native MDH and the stabilized PEPC.

What is claimed is:

1. A liquid, time stable, single assay reagent for the determination of carbon dioxide in serum and body fluids under alkaline conditions which comprises an aqueous solution of (a) a reactively stabilized phosphoenolpyruvate carboxylase and a first diagnostic substrate present in a diagnostically effective amount sufficient to react with bicarbonate ion in the presence of the reactively stabilized phosphoenolpyruvate carboxylase to form a product which will react with a second substrate selected from the group consisting of reduced nicotinamide adenine dinucleotide and reduced nicotinamide adenine dinucleotide phosphate:

(b) a diagnostically effective amount of the second substrate, (c) a diagnostically effective amount of a second diagnostic enzyme to form the oxidized form of the second substrate by reaction of the second substrate with the product, and (d) at least one stabilizing enzyme and a corresponding substrate for said stabilizing enzyme present in an amount sufficient to inhibit oxidation of the second substrate but insufficient to prevent measurement of oxidize form of the second substrate upon reaction of the second substrate with the product to form the oxidized form of the second substrate as a measure of carbon dioxide in a sample of sera, said solution having a pH of from about 5 to about 11.

2. The assay reagent as claimed in claim 1 in which there is provided a cofactor to further stabilize the reactively stabilized phosphoenolpyruvate carboxylase is present.

3. The assay reagent as claimed in claim 2 in the co-factor is d-biotin.

4. The assay reagent as claimed in claim 1 which further contains a second stabilizer for the second substrate selected from the group consisting of polyols, gelatin and mixtures thereof.

5. The assay reagent as claimed in claim 1 in which the first diagnostic substrate is phosphoenol pyruvate.

6. The assay reagent as claimed in claim 1 in which the second diagnostic enzyme is malate dehydrogenase.

7. The assay reagent as claimed in claim 5 in which the second diagnostic enzyme is malate dehydrogenase.

8. The assay reagent as claimed in claim 1 in which the stabilizing enzyme for the second substrate is hexokinase and the corresponding substrate is a mixture of glucose and glucose-6-phosphate.

9. The assay composition as claimed in claim 8 in which there is provided magnesium ion for control of hexokinase and a chelating agent for magnesium.

10. The assay composition as claimed in claim 4 in which there is provided adenosine-5'-triphosphate as an additional stabilizer for the second substrate.

11. The assay composition as claimed in claim 1 in which the solution pH is maintained by a Zwitterionic buffer.

12. A liquid, time-stable, single reagent composition for the determination of carbon dioxide in serum which comprises a carbon-dioxide-free aqueous solution comprising from about 0.1 to about 100 g/l buffer, from about 0.001 to about 10 g/l of a chelating agent for magnesium, from about 0.1 to about 100 g/l glucose, from about 0.1 to about 100 g/l phosphoenolpyruvate tri(cyclohexylammonium) salt, from 0.01 to about 50 g/l adenosine-5-triphosphate, from 0.01 to about 5 g/l d-biotin, from 0 to 200 ml/l of a mixture of sorbitol and gelatin, from 0.6 to about 2 g/l nicotinamide adenine dinucleotide, from about 2 to about 2000 U/l hexokinase as determined at 25° C., from 0.1 to about 5000 U/l glucose-6-phosphate dehydrogenase determined at 25° C., from 200 to about 5000 U/l malate dehydrogenase, from about 200 to about 5000 U/l stabilized phosphoenolpyruvate carboxylase determined at 37° C., said composition having a pH of from about 5 to about 11.

13. The composition as claimed in claim 12 in which the solution has a pH of about 8.7 to about 9.5.

14. The composition as claimed in claim 12 in which the buffer is a Zwitterionic buffer.

15. The composition as claimed in claim 13 in which the buffer is a Zwitterionic buffer.

16. The composition as claimed in claim 14 in which the Zwitterionic buffer is tris(hydroxymethylamino ethane).

17. The composition as claimed in claim 15 in which the Zwitterionic buffer is tris(hydroxymethylamino ethane).

18. The composition as claimed in claim 12 in which there is present a microbial stabilizer.

19. The composition as claimed in claim 12 in which the microbial stabilizer is sodium azide present in an amount of from about 0.01 to about 20 g/l.

20. A time-stable single reagent for the determination of carbon dioxide in serum which comprises a aqueous solution comprising from about 0.4 to about 2 g/l tris (hydroxymethylamino ethane), from about 0.2 to about 1 g/l ethylenediaminetetraacetic acid, from about 2 to about 10 g/l glucose, from about 0.5 to about 20 g/l phosphoenolpyruvatetri(cyclohexylammonium) salt, from 0.5 to about 2.5 g/l adenosine-5-triphosphate, from 0.4 to about 2 g/l sodium azide, from about 0.64 to about 3.2 g/l of magnesium acetate, from 0.24 to 1.2 g/l d-biotin, about 40 ml/l of a mixture of sorbitol and gelatin, from 1.3 to about 6.5 g/l nicotinamide adenine dinucleotide, from about 200 to about 1000 U/l hexokinase as determined at 25° C., from 20 to about 100 U/l glucose-6-phosphate dehydrogenase determined at 25° C., from 500 to about 2500 U/l malate dehydrogenase, from about 500 to about 2500 U/l reactively stabilized phosphoenolpyruvate carboxylase determined at 37° C., said composition having a pH of from about 8.75 to about 9.25.

21. In a liquid assay reagent for the determination of carbon dioxide in a fluid sample selected from serum and body fluids under alkaline conditions which comprises an aqueous solution having a pH of from about 5 to about 15 containing phosphoenolpyruvate carboxylase, a first diagnostic substrate present in a diagnostically effective amount sufficient to react with bicarbonate ion in the presence of phosphoenolpyruvate carboxylase to form a product which will react with a second substrate selected from the group consisting of reduced nicotinamide adenine dinucleotide and reduced nicotinamide adenine dinucleotide phosphate, a diagnostically effective amount of the second substrate, a diagnostically effective amount of a second diagnostic enzyme provided to form the oxidized form of the second substrate by reaction of the second substrate with the product, the improvement which comprises, in combination, providing phosphoenolpyruvate carboxylase as reactively stabilized phosphoenolpyruvate carboxylase and at least one stabilizing enzyme and a corresponding substrate for said stabilizing enzyme present in an amount sufficient to inhibit oxidation of the second substrate but insufficient to prevent measurement of oxidized form of the second substrate upon reaction of the second substrate with the product to form the oxidized form of the second substrate as a measure of carbon dioxide in the fluid sample, to form a liquid assay which is stable for at least 1 day at 41° C.

* * * * *